United States Patent
Foley et al.

(10) Patent No.: US 9,840,449 B2
(45) Date of Patent: *Dec. 12, 2017

(54) GUERBET ALCOHOLS AND METHODS FOR PREPARING AND USING SAME

(71) Applicant: P2 Science, Inc., New Haven, CT (US)

(72) Inventors: Patrick Foley, New Haven, CT (US); Yonghua Yang, New Haven, CT (US)

(73) Assignee: P2 SCIENCE, INC., New Haven, CT (US)

(*) Notice: Subject to any disclaimer, the term of this patent is extended or adjusted under 35 U.S.C. 154(b) by 575 days.

This patent is subject to a terminal disclaimer.

(21) Appl. No.: 13/801,209

(22) Filed: Mar. 13, 2013

(65) Prior Publication Data

US 2013/0274511 A1    Oct. 17, 2013

Related U.S. Application Data

(60) Provisional application No. 61/613,867, filed on Mar. 21, 2012, provisional application No. 61/641,742, filed on May 2, 2012, provisional application No. 61/662,639, filed on Jun. 21, 2012.

(51) Int. Cl.

| | | |
|---|---|---|
| C07C 45/40 | (2006.01) |
| C07C 29/141 | (2006.01) |
| C07C 47/02 | (2006.01) |
| C07C 31/125 | (2006.01) |
| C07C 59/245 | (2006.01) |
| C07C 45/74 | (2006.01) |
| C07C 45/82 | (2006.01) |

(52) U.S. Cl.
CPC .......... *C07C 29/141* (2013.01); *C07C 31/125* (2013.01); *C07C 45/40* (2013.01); *C07C 45/74* (2013.01); *C07C 45/82* (2013.01); *C07C 47/02* (2013.01); *C07C 59/245* (2013.01)

(58) Field of Classification Search
CPC ............................ C07C 1/207; C07C 45/40
USPC .......................................... 562/582; 568/392
See application file for complete search history.

(56) References Cited

U.S. PATENT DOCUMENTS

| | | |
|---|---|---|
| 2,813,113 A | 11/1957 | Goebel et al. |
| 2,875,241 A | 2/1959 | Miller et al. |
| 3,119,880 A | 1/1964 | John et al. |
| 3,558,716 A | 1/1971 | Engelhardt et al. |
| 3,864,407 A | 2/1975 | Yates |
| 3,979,466 A | 9/1976 | Yates |
| 4,425,458 A | 1/1984 | Lindner |
| 4,426,542 A | 1/1984 | Barker et al. |
| 4,540,828 A | 9/1985 | Yang |
| 4,731,190 A | 3/1988 | O'Lenick, Jr. et al. |
| 4,767,815 A | 8/1988 | O'Lenick, Jr. |
| 4,800,077 A | 1/1989 | O'Lenick, Jr. et al. |
| 4,830,769 A | 5/1989 | O'Lenick, Jr. et al. |
| 5,094,667 A | 3/1992 | Schilowitz et al. |
| 5,264,006 A | 11/1993 | Schilowitz et al. |
| 5,312,968 A | 5/1994 | O'Lenick, Jr. et al. |
| 5,387,374 A | 2/1995 | Westfechtel et al. |
| 5,488,121 A | 1/1996 | O'Lenick, Jr. |
| 5,646,321 A | 7/1997 | O'Lenick, Jr. |
| 5,717,119 A | 2/1998 | O'Lenick, Jr. |
| 5,744,626 A | 4/1998 | O'Lenick, Jr. |
| 5,756,785 A | 5/1998 | O'Lenick, Jr. |
| 5,786,389 A | 7/1998 | O'Lenick, Jr. et al. |
| 5,919,743 A | 7/1999 | O'Lenick, Jr. |
| 5,919,959 A | 7/1999 | O'Lenick, Jr. |
| 5,929,263 A | 7/1999 | O'Lenick, Jr. |
| 6,008,181 A | 12/1999 | Cripe et al. |
| 6,013,813 A | 1/2000 | O'Lenick, Jr. |
| 6,060,443 A | 5/2000 | Cripe et al. |
| 6,093,856 A | 7/2000 | Cripe et al. |
| 6,309,521 B1 | 10/2001 | Andrews et al. |
| 6,768,029 B1 | 7/2004 | Khan et al. |
| 9,035,091 B2 | 5/2015 | Foley |
| 2002/0061566 A1 | 5/2002 | Eirich et al. |
| 2007/0276165 A1 | 11/2007 | Gutsche |
| 2009/0101519 A1 | 4/2009 | Szalay et al. |
| 2011/0282108 A1 | 11/2011 | Ko et al. |
| 2013/0165685 A1 | 6/2013 | Hannen et al. |
| 2013/0177497 A1 | 7/2013 | Fitch et al. |

FOREIGN PATENT DOCUMENTS

| | | |
|---|---|---|
| DE | 3440620 A1 | 5/1986 |
| DE | 10232458 A1 | 7/2003 |
| EP | 0095562 | 7/1983 |
| EP | 2390242 A2 | 11/2011 |
| JP | S32-010666 B | 12/1957 |
| JP | H01-268655 A | 10/1989 |
| JP | 2001-340763 A | 12/2001 |
| JP | 2005-298488 A | 10/2005 |
| JP | 2007-262019 A | 10/2007 |
| JP | 2010-065020 A | 3/2010 |
| JP | 2010-180197 A | 8/2010 |
| WO | WO 00/78699 A1 | 12/2000 |
| WO | WO 02/48431 A2 | 6/2002 |

(Continued)

OTHER PUBLICATIONS

Cahn, R.S., "Specification of Molecular Chirality", *Angew. Chem. Inter. Edit.* 5, 385-415 (1966), (errata 1966: 5, 511).

Cahn, R.S., et al., "Specification of Configuration about Quadricovalent Asymetric Atoms", *Journal of the Chemical Society*, pp. 612-622 (1951).

Cahn, R.S. et al., "The Specification of Asymmetric Configuration in Organic Chemistry", *Experientia*, vol. XII, vol. 3, pp. 81-94 (1956).

(Continued)

*Primary Examiner* — Yong Chu
*Assistant Examiner* — Sonya Wright
(74) *Attorney, Agent, or Firm* — Hoxie & Associates LLC

(57) ABSTRACT

The invention relates to Guerbet alcohol precursors and Guerbet alcohols, as well as to processes for synthesizing them.

12 Claims, 3 Drawing Sheets

(56) References Cited

FOREIGN PATENT DOCUMENTS

| WO | WO 2008/084062 A1 | 7/2008 |
|---|---|---|
| WO | WO 2010/082793 A2 | 7/2010 |
| WO | WO 2011/054483 A1 | 5/2011 |

OTHER PUBLICATIONS

Cahn, R.S., "An introduction to the sequence rule: A system for the specification of absolute configuration", *Journal of Chemical Education*, 41(3):116-125 (1964).
Geissman, T.A., "The Cannizzaro Reaction", *Organic Reactions*, vol. II, Chapter 3, pp. 94-113 (1944).
Matsu-Ura, Toyomi et al., "Guerbet Reaction of Primary Alcohols Leading to β-Alkylated Dimer Alcohols Catalyzed by Iridium Complexe", *Journal of Organic Chemistry*, 71:8306-8308 (2006).
O'Lenick, Jr., "Guerbet Chemistry", *Journal of Surfactants and Detergents*, 4(3):311-315 (2001).
O'Lenick, Jr., Anthony J., "A review of Guerbet Chemistry", www.zenitech.com/documents/guerbet chemistry.pdf, Accessed Mar. 16, 2012.
Omonov, Tolibjon S., et al., "Ozonolysis of Canola Oil: A Study of Product Yields and Ozonolysis Kinetics in Different Solvent Systems", *Journal of the American Oil Chemists' Society*, 88:689-705 (2011) DOI 10.1007/s11746-010-1717-4.
Sunwoo, Chunhee K., et al., "Optimal Surfactant Structures for Cosurfactant-Free Microemulston Systems I. $C_{16}$ and $C_{14}$ Guerbet Alcohol Hydrophobes", *J. Dispersion Science and Technology*, 13(5):491-514 (1992).
Throckmorton, P.E., et al., "Pilot Run, Plant Design and Cost Analysis for Reductive Ozonolysis of Methyl Soyate", *Journal of the American Oil Chemists' Society*, 49(11):643-648 (1972).
Veibel, S., et al., "On the Mechanism of the Guerbet Reaction," *Tetrahedron*, 23:1723-1733 (1967).
Adams, T.C. et al., "7-Amino-5-(methylamino)heptanoic acid: A potential putrescine hapten", J. Org. Chem., American Chemical Society, vol. 46, No. 22, Jan. 1, 1981, pp. 4582-4584, XP002633808.
Ballini, R. and Rinaldi, A., "Michael addition of nitroalkanes to dimemethyl maleate with DBU. A new direct method for the synthesis of polyfunctionalized alpha,beta-unsaturated esters", Tetrahedron Letters, Pergamon, GB, vol. 35, No. 49, Dec. 5, 1994, pp. 9247-9250, XP027397061.
Ballini, R. and Palmieri, A., "Potassium Fluoride/Basic Alumina as Far Superior Heterogeneous Catalyst for the Chemoselective Conjugate Addition of Nitroalkanes to Electron-Poor Alkenes Having Two Electron-Withdrawing Groups in [alpha]- and [beta]-Positions", Adv. Syn. & Cat., vol. 348, No. 10-11, Jul. 1, 2006, pp. 1154-1156, XP55189361.
Chem. Abs. AN: 1961 :32702 & Nippon Kagaku Zasshi, vol. 81, pp. 272-274 (1960), XP002739667.
Matsuura, Toyomi et al., "Guerbet reaction of primary alcohols leading to beta-alkylated dimer alcohols catalyzed by iridium complexes", J. Org. Chem., 2006, vo. 71, pp. 8306-8308.
Molinari, E. et al., "Die Zersetzungsprodukte des Olsaure-ozonids", Berichte Der Deutschen Chemischen Gesellschaft, vol. 41, No. 2, May 1, 1908, pp. 2794-2799, XP55189330, ISSN: 0365-9496, DOI: 10.1002/cber.190804102225.
International Search Report and Written Opinion dated Jun. 21, 2013, in corresponding International Application No. PCT/US2013/030962.
European Extended Search Report dated May 27, 2015, in corresponding EP Application No. 13764490.2.
Maggiolo A. "Ozonization of Fatty Acids and Their Derivatives", *The Journal of the American Oil Chemists' Society*, (Apr. 1963), vol. 40, p. 161-164.
Piacenti, F. et al. "Aldol condensation of Y-formylbutyric acid esters," *Gazzetta Chimica Italiana*, vol. 98 (1968):235-44.
Ducher, S. "Contribution a l'etude du butenolide. Reaction d'alcoolyse" *Bulletin de la Societe Chimique de France* (1959):1259-67.
Pryde, E. H. et al. "Ozonization of Soybean Oil. The Preparation and Some Properties of Aldehyde Oils," *J. Am. Oil Chem. Soc.*, 1961, vol. 38(7), pp. 375-379.

GUERBET ALCOHOLS AND METHODS FOR PREPARING AND USING SAME

RELATED APPLICATIONS

This application claims priority to, and the benefit of, U.S. provisional application Nos. 61/613,867, filed Mar. 21, 2012; 61/641,742, filed May 2, 2012; and 61/662,639, filed Jun. 21, 2012; the contents of each are incorporated herein by reference in their entireties.

BACKGROUND OF THE INVENTION

Guerbet Alcohols (GA) or Guerbet-type alcohols are used as synthetic reagents and formulation ingredients for a number of personal care and cleaning products. Guerbet Alcohols are known to have desirable physical properties such as very low melting points and low viscosities as compared to linear alcohols of similar molecular weight. See, e.g., O'Lenick, *Journal of Surfactants and Detergents*, vol. 4(3), 311-315, 2001.

Currently, the practice for making Guerbet-type alcohols involves either: (1) hydroformylation of α-olefins to make aldehydes that can then be dimerized and/or reduced (see, e.g., WO2010082793), or (2) the heating of alkyl alcohols (>130° C.) over basic catalyst to generate alkyl aldehydes in situ, which then dimerize and can later be reduced (see, e.g., WO2010082793). In the case of the first process, the α-olefins are generally derived from resource depleting petrochemical feedstocks, and in the case of second process, the alcohols have to be heated to high temperatures and thus significant energy is required. Therefore, an energy efficient method for the production of alkyl aldehydes and Guerbet alcohols from non-depleting resources is desired. The present invention addresses the needs.

SUMMARY OF THE INVENTION

In one aspect, the invention relates to a method of synthesizing an enal of formula I or a salt thereof:

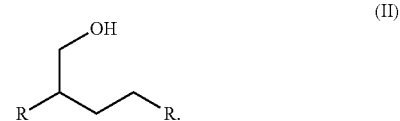

In this formula, R is hydrogen or unsubstituted or substituted $C_1$-$C_{20}$ alkyl, wherein the alkyl is linear or branched and optionally contains a carbonyl moiety (C=O) within or at the terminus of the alkyl and is optionally substituted with $OR_a$, $COOR_a$, $NR_aR_b$, $S(O)_pR_a$, $CONR_aR_b$, or $NR_aCOR_b$, p being 0, 1, or 2, and each of $R_a$ and $R_b$, independently, being H, $C_1$-$C_{10}$ alkyl, $C_3$-$C_8$ cycloalkyl, aryl, or heteroaryl.

The method includes (1) ozonolysis of a triglyceride, a fatty acid, or a fatty acid ester to obtain a mono-aldehyde having the formula R—$CH_2$CHO; and (2) dimerizing the mono-aldehyde to obtain the compound of formula I.

The conversion of triglyceride oils into value-added materials is a primary activity of the oleochemical industry. The treatment of vegetable oils with ozone to cleave sites of unsaturation in the triglyceride alkyl chains has long been used to generate useful products, such as mono- and difunctionalized alkanes. See, e.g., Throckmorton, et al., *Journal of the American Oil Chemists' Society*, Vol. 49, 643-648, 1972. This process is known as ozonolysis and continues to be of interest to this day. See, e.g., Omonov, et al. *Journal of the American Oil Chemists' Society*, Vol. 88, 689-705, 2011. Also of interest has been the use of ozonolysis to generate alkyl aldehydes from vegetable oils. Alkyl aldehydes have use as chemical building blocks, fragrances, and food additives.

This invention relates to use of alkyl aldehydes from ozonolysis of biologically derived triglycerides (TG), fatty acids (FA), or fatty acid esters (FAE) to generate Guerbet alcohol precursors (GAP), e.g., enal compounds. These enals can then be reduced to give branched alcohols, sometimes referred to as Guerbet Alcohols (GA).

In certain compounds of the invention, R is an aliphatic chain of a fatty acid. In certain compounds, R is $C_1$-$C_{20}$ alkyl having 1, 2, 3, 4, 5, 6, 7, 8, 9, 10, 11, 12, 13, 14, 15, 16 17, 18, 19, or 20 carbon atoms, for example 2, 3, 4, 5, 6, 7, 8, 9, or 10 carbon atoms, or for example 6, 7, 8, 9, or 10 carbon atoms, or for example, 11, 12, 13, 14, 15, 16, 17, 18, 19, or 20 carbon atoms.

In one embodiment, the method further includes reducing the enal compound of formula I to produce a compound of formula II or a salt thereof:

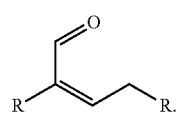

For example, the reduction is performed in the presence of a hydrogenation catalyst.

For example, the method includes (1) ozonolysis of a triglyceride, a fatty acid, or a fatty acid ester to obtain a mono-aldehyde having the formula R—$CH_2$CHO; (2) isolating the mono-aldehyde from other ozonolysis products by distillation, e.g., distillation under vacuum; and (3) dimerizing the mono-aldehyde to obtain the compound of formula I.

For example, the dimerization reaction of the synthetic method described herein is performed in the presence of an acid or base, such as acidic or basic solid-phase ion exchange catalysts.

For example, the dimerization reaction of the synthetic method described herein is performed in an aqueous solution containing an alcohol (e.g., an alcohol aqueous solution). The alcohol can either be a primary or secondary alcohol, e.g., ethanol, methanol, propanol, isopropanol, or butanol.

For example, the dimerization reaction of the synthetic method described herein is performed in a polar solvent (e.g., a polar protic or polar aprotic solvent) such as an aqueous solution. For example, when R in the mono-aldehyde R—$CH_2$CHO is $C_1$-$C_{20}$ alkyl containing a carboxyl moiety (COOH) at the terminus of the alkyl, the dimerization is performed in an aqueous solution. The aqueous solution may contain or be free of alcohol.

For example, the volume ratio between the alcohol and water in the alcohol aqueous solution ranges from 10:1 to 1:10, e.g., between 3:1 and 1:3, between 2:1 and 1:2, or about 1:1.

For example, the dimerization reaction of the synthetic method described herein is performed in an alcohol aqueous solution at a temperature below 100° C., e.g., between 50 and 90° C. or between 60 and 80° C.

For example, the ozone used in the ozonolysis step of the synthetic method described herein is generated by electrolyzing water.

For example, the hydrogen generated by electrolysis of water is used in the reduction step of the synthetic method described herein to generate the compound of formula II.

In one embodiment, R is hydrogen, unsubstituted $C_1$-$C_{20}$ alkyl, or substituted $C_1$-$C_{20}$ alkyl containing —COOH at the terminus of the alkyl chain. For example, the unsubstituted $C_1$-$C_{20}$ alkyl or the substituted $C_1$-$C_{20}$ alkyl containing the terminal —COOH is a linear alkyl. For example, the unsubstituted $C_1$-$C_{20}$ alkyl or the substituted $C_1$-$C_{20}$ alkyl containing the terminal —COOH is a branched alkyl. For example, the substituted $C_1$-$C_{20}$ alkyl containing the terminal —COOH is optionally further substituted with one or more groups selected from $OR_a$, $COOR_a$, $NR_aR_b$, $S(O)_pR_a$, $CONR_aR_b$, and $NR_aCOR_b$.

In one embodiment, the method further includes derivatizing the compound of formula I to produce a compound of formula III:

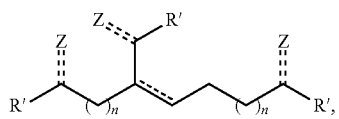

(III)

or a salt thereof, wherein
- - - - - is a single or double bond,
each - - - - - is a double bond or absent,
each Z independently is O or S when - - - - - is a double bond, or Z is absent when - - - - - is absent,
each R' independently is $OR_a$ or $NR_aR_b$, each of $R_a$ and $R_b$, independently, being H, $C_1$-$C_{10}$ alkyl, $C_3$-$C_8$ cycloalkyl, aryl, or heteroaryl, and
n is 1, 2, 3, 4, 5, 6, 7, 8, 9, 10, 11, or 12.

For example, R in formula I is $C_1$-$C_{20}$ alkyl containing —COOH at the terminus of the alkyl chain.

For example, the derivatization of a compound of formula I includes reduction, oxidation, amidization, exchanging S and O atoms to form thioketones, and/or forming a salt.

For example, the compound of formula III does not contain any Z group.

For example, the compound of formula III contains two Z groups.

For example, the compound of formula III contains three group.

The invention also relates to an enal compound of formula I, a compound of formula II or III, or a salt thereof, generated by the synthetic methods described herein.

The invention also relates to a compound of formula IV below:

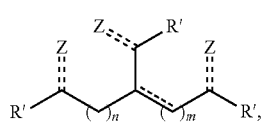

(IV)

or a salt thereof, wherein
- - - - - is a single or double bond,
each - - - - - is a double bond or absent,
each Z independently is O or S when - - - - - is a double bond, or Z is absent when - - - - - is absent,
each R' independently is $OR_a$ or $NR_aR_b$, each of $R_a$ and $R_b$, independently, being H, $C_1$-$C_{10}$ alkyl, $C_3$-$C_8$ cycloalkyl, aryl, or heteroaryl, and each of m and n, independently, is 1, 2, 3, 4, 5, 6, 7, 8, 9, 10, 11, or 12.

Also contemplated is a method of synthesizing a compound of formula (IV) above. The method includes reacting $R_x$—$CH_2CHO$ with $R_y$—$CH_2CHO$, in which each $R_x$ and $R_y$, independently is substituted $C_1$-$C_{20}$ alkyl containing —COOH at the terminus of the alkyl chain. $R_x$ and $R_y$ can be the same or different. The method may further include reduction, oxidation, amidization, exchanging S and O atoms to form thioketones, and/or forming a salt.

For example, the salt of a compound of any of formulae I-IV, is formed by reacting a —COOH group of the compound with a base to form alkali metal salts such as $Na^+$, $K^+$, $Li^+$, alkali earth metal salts such as $Mg^{2+}$ or $Ca^{2+}$, organic amine salts, or organic phosphonium salts.

The compounds described herein can find utility in a variety of applications where multi-functionality compounds are desired. These applications include polymers such as nylon, polyester, and polyurethane, as well as lubricants.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. In addition, the materials, methods, and examples are illustrative only and are not intended to be limiting.

Other features and advantages of the invention will be apparent from the following detailed description and claims.

DETAILED DESCRIPTION OF THE INVENTION

Figure 1:
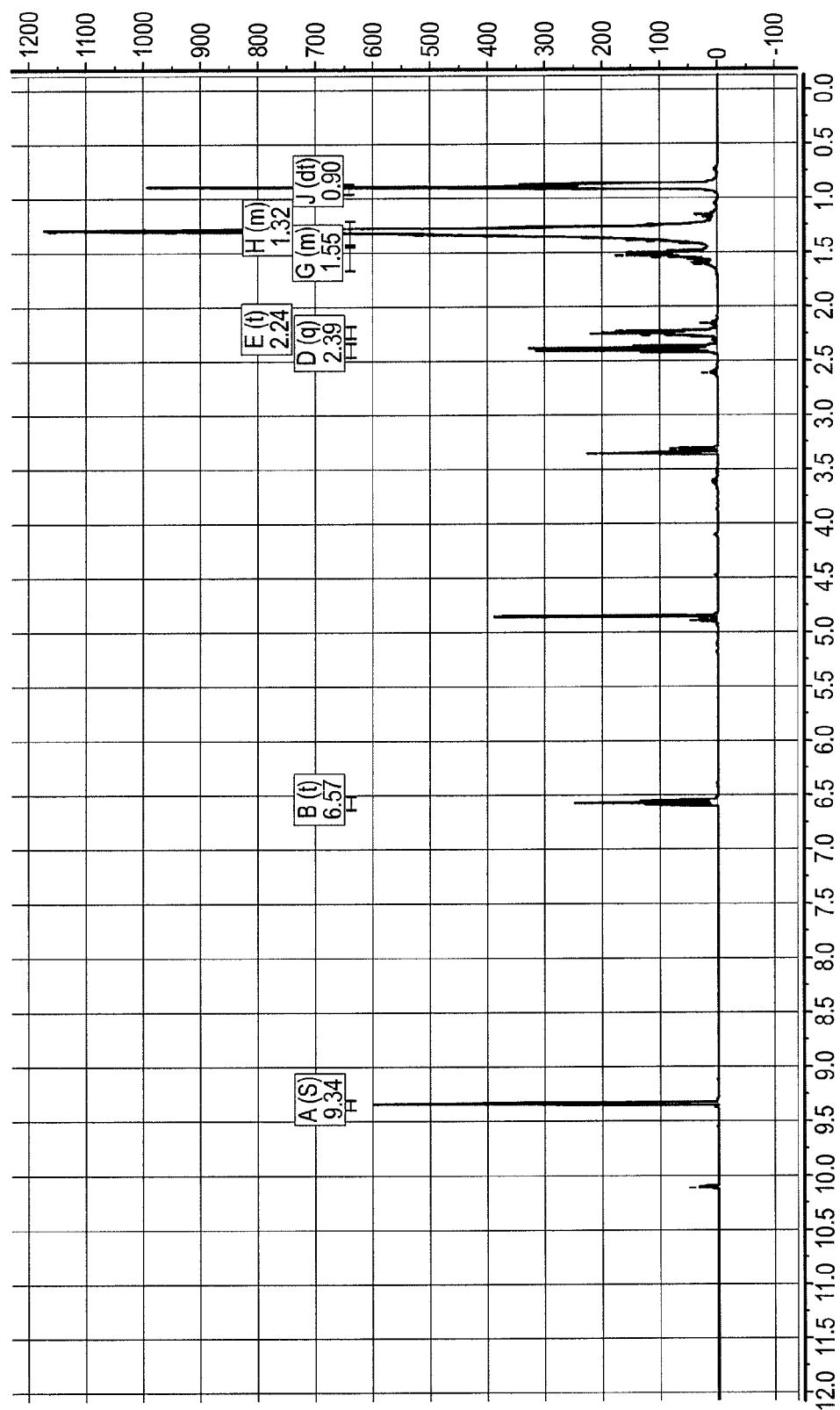
FIG. 1 is a $^1H$ NMR spectrum of the product resulting from the dimerization of nonanal.

The invention relates to novel methods of synthesizing Guerbet alcohol precursors and Guerbet alcohols, and the products from the processes. In one aspect, the invention relates to a method of synthesizing an enal of formula I or a salt thereof:

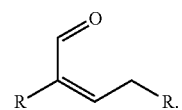

(I)

In this formula, R is hydrogen or unsubstituted or substituted $C_1$-$C_{20}$ alkyl, wherein the alkyl is linear or branched and optionally contains a carbonyl moiety (C═O) within or at the terminus of the alkyl and is optionally substituted with $OR_a$, $COOR_a$, $NR_aR_b$, $S(O)_pR_a$, $CONR_aR_b$, or $NR_aCOR_b$, p being 0, 1, or 2, and each of $R_a$ and $R_b$, independently, being H, $C_1$-$C_{10}$ alkyl, $C_3$-$C_8$ cycloalkyl, aryl, or heteroaryl.

The synthetic method described herein includes ozonolysis of a triglyceride, a fatty acid, or a fatty acid ester to obtain a mono-aldehyde having the formula R—CH$_2$CHO; and dimerizing the mono-aldehyde to obtain the compound of formula I.

In one embodiment, the synthetic method described herein further includes reducing the enal compound of formula I to produce a compound of formula II or a salt thereof:

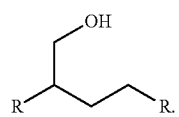
(II)

In one embodiment, R is hydrogen, unsubstituted C$_1$-C$_{20}$ alkyl, or substituted C$_1$-C$_{20}$ alkyl containing —COOH at the terminus of the alkyl chain.

In one embodiment, R is substituted C$_1$-C$_{20}$ alkyl containing —COOH at the terminus of the alkyl chain and the method further includes derivatizing the compound of formula I to produce a compound of formula III:

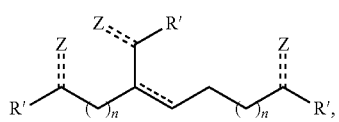
(III)

or a salt thereof, wherein

----- is a single or double bond, each ----- is a double bond or absent, each Z independently is O or S when ----- is a double bond, or Z is absent when ----- is absent, each R' independently is OR$_a$ or NR$_a$R$_b$, each of R$_a$ and R$_b$, independently, being H, C$_1$-C$_{10}$ alkyl, C$_3$-C$_8$ cycloalkyl, aryl, or heteroaryl, and n is 1, 2, 3, 4, 5, 6, 7, 8, 9, 10, 11, or 12.

For example, the derivatization of a compound of formula I includes reduction, oxidation, amidization, exchanging S and O atoms to form thioketones, and/or forming a salt.

For example, the compound of formula III is a compound of formula IIIa, IIIb or IIIc below:

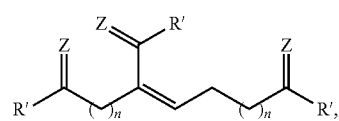
(IIIa)

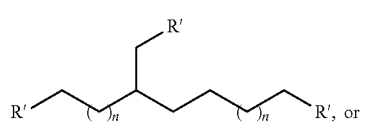
(IIIb)

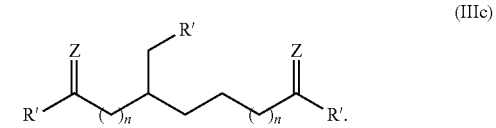
(IIIc)

For example, the reduction of a compound of formula I is performed in the presence of a suitable hydrogenation catalyst. The hydrogenation catalysts can be homogeneous or heterogeneous catalysts. Examples of catalysts include but are not limited to platinum, palladium (e.g., U.S. Pat. No. 3,979,466), rhodium, ruthenium, nickel, lead salts (e.g., U.S. Pat. No. 3,119,880), oxides of copper, lead, zinc, chromium, molybdenum, tungsten, manganese (e.g., U.S. Pat. No. 3,558,716), and silver compounds (e.g., U.S. Pat. No. 3,864,407).

For example, the synthetic method described herein further includes (1) ozonolysis of a triglyceride, a fatty acid, or a fatty acid ester to obtain a mono-aldehyde having the formula R—CH$_2$CHO; (2) isolating the mono-aldehyde from other ozonolysis products by distillation, e.g., distillation under vacuum; and (3) dimerizing the mono-aldehyde to obtain the compound of formula I.

For example, the dimerization reaction of the synthetic method described herein is performed in the presence of an acid or base, such as acidic or basic solid-phase ion exchange catalysts. Examples of catalysts include but are not limited to, boron trifluoride, amine catalysts such as pyrrolidine, morpholine or piperidine. Each of the catalysts above can be either free or resin-bound. Transition metal catalysts and/or zeolites can be used as well.

For example, the ozone used in the ozonolysis step of the synthetic method described herein is generated by electrolyzing water.

For example, the hydrogen generated by electrolysis of water is used in the reduction step of the synthetic method described herein to generate the compound of formula II.

An example of the methods of the invention is illustrated as in Scheme 1 below.

Scheme 1

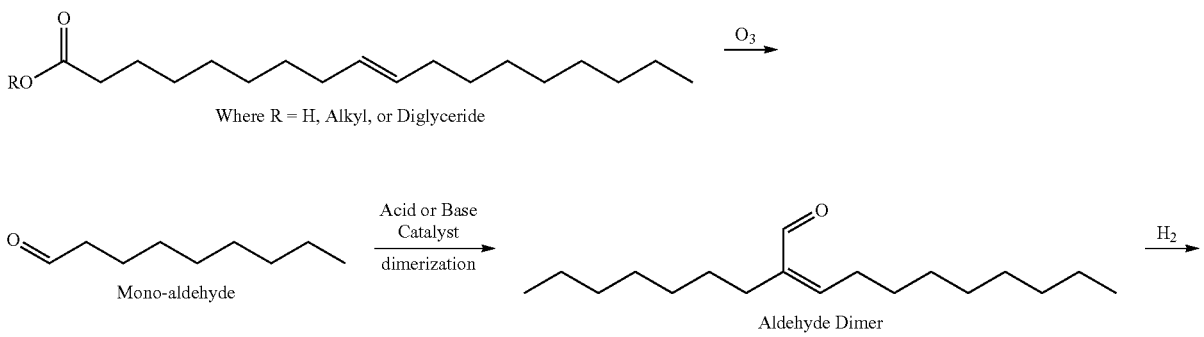

-continued

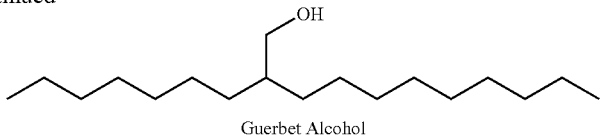
Guerbet Alcohol

The dimerization of aliphatic aldehydes to generate enals is an important industrial transformation in the route to produce Guerbet Alcohols (GA). Currently, aldehydes are either generated from alcohols over a basic dehydrogenation catalyst in situ and are then dimerized at high temperatures, or they are dimerized directly from hydroformylated olefins. In the case of the latter, short-chain (3-5 carbons) aliphatic aldehydes are generally reacted in dilute basic aqueous solutions in the presence of 1-5% base (e.g., NaOH) at dilutions ranging from 9:1 through 20:1, basic solution: aldehyde volumetric ratio [Bahrmann, H., et al., 2-*Ethyl Hexanol: Ullmann's Encyclopedia of Industrial Chemistry*. Vol. 13, 579-584, 2012 Wiley-VCH Verlag GmbH & Co. KGaA, Weinheim]. The advantage to this process is that the starting aldehydes are soluble in the basic solutions and can therefore react readily, but the enal products that are formed upon dimerization are not soluble, and therefore the desired products are much slower to react and can be isolated by simple phase separation.

While it might be desirable to apply these conditions to aldehydes derived from the ozonolysis of vegetable oils, such as hexanal and nonanal, similarly desirable conversions and separations were not achieved following the method described above, owing to the insolubility of the longer chain aliphatic aldehydes in the aqueous medium. Accordingly, new solvent systems and conditions are needed for the dimerization of longer chain aldehydes. Current invention addresses this.

The invention also relates to a process for the dimerization of aldehydes (e.g., oleochemical-derived aldehydes, specifically, those having a chain length longer than five carbons) using an alcohol aqueous solution as reaction media to obtain enal products with high yields (e.g., no less than 90% conversion ratio). Specifically, starting aldehydes are first solubilized in a basic reaction media and are then converted to the target dimer successfully in high yield. Following conversion, the desired products can be quickly phase separated from the reaction media for facile isolation.

In Scheme 1 above, the dimerization reaction of the disclosed method can be performed in an aqueous solution containing an alcohol, e.g., an alcohol aqueous solution, in which the alcohol is, for example, ethanol, methanol, propanol, isopropanol, or butanol. The volume ratio between the alcohol and water can range from 10:1 to 1:10, e.g., between 3:1 and 1:3, between 2:1 and 1:2, or about 1:1. The dimerization reaction can be performed at a temperature below 100° C., e.g., between 50 and 90° C. or between 60 and 80° C.

In one embodiment, an aldehyde (e.g., $C_{6-12}$ aldehyde) is added to a solvent (e.g., an ethanol aqueous solution) charged with a base (e.g., NaOH) at a temperature below 100° C. (e.g., 70° C.). The volume ratio between the solvent and the aldehyde can range from 0.5:1 to 10:1 (e.g., between 1:1 and 9:1, between 1:1 and 4:1, or between 1:1 and 2:1). The mixture is vigorously stirred (e.g., via overhead stirring at 660 RPM) for at least fifteen minutes at 70° C. To determine reaction completion, an aliquot of the reaction mixture is removed and quenched into, e.g., 1.0 M hydrochloric acid. The aliquot is diluted with water and the organics are extracted with deuterated chloroform, from which proton NMR is taken. If most of the starting material (e.g., no less than 90%, no less than 80%, or no less than 70%) has been converted to the desired enal product as determined by NMR, the remaining reaction mixture is subsequently poured into a graduated cylinder and observation of reaction mixture phase separation is noted.

In one embodiment, the dimer product enal is then reduced to the desired alcohol by hydrogenation in the presence of a suitable catalyst, such as Raney Nickel. For example, nonanal is dimerized according to the aforementioned methods, and the resulting dimer can be separated from the alcohol and water layer before the reduction reaction. The dimer product can be charged with Raney Nickel (e.g., 10%-30%, 15-25%, or 20% wt/wt) and the resulting mixture can be placed in a high pressure reactor, and vigorously stirred under a high pressure of $H_2$ and a high temperature (e.g., under about 300-500 psi of $H_2$ and at about 120-200° C.) for about 3-24 hours to obtain the desired alcohol product. The alcohol product from the reduction reaction can be >80% pure (e.g., >90%, >95%, >98%, or >99% pure) with >70% yield (e.g., >75%, >80%, >85%, >90%, >95%, >98%, or >99% yield). $^1$H NMR and gas chromatography can be used to characterize the desired alcohol product. For example, disappearance of the enal protons and the appearance of 2 methylene protons at ~3.3-3.5 ppm in $^1$H NMR can show the conversion of the dimer starting material to the desired alcohol product. For example, the alcohol product is free of undesired byproduct or starting material. For example, the impurities (e.g., undesired byproduct or starting material such as the aldehyde dimer) in the alcohol product is less than 20% (e.g., <10%, <5%, <2%, or <1%).

The invention also relates to the integration of the process into a greater ozonolysis process scheme, where some but not all of the TG/FA/FAE material is used for the production of GAP/GA. A representative integrated process scheme is shown in Scheme 2 below.

Scheme 2

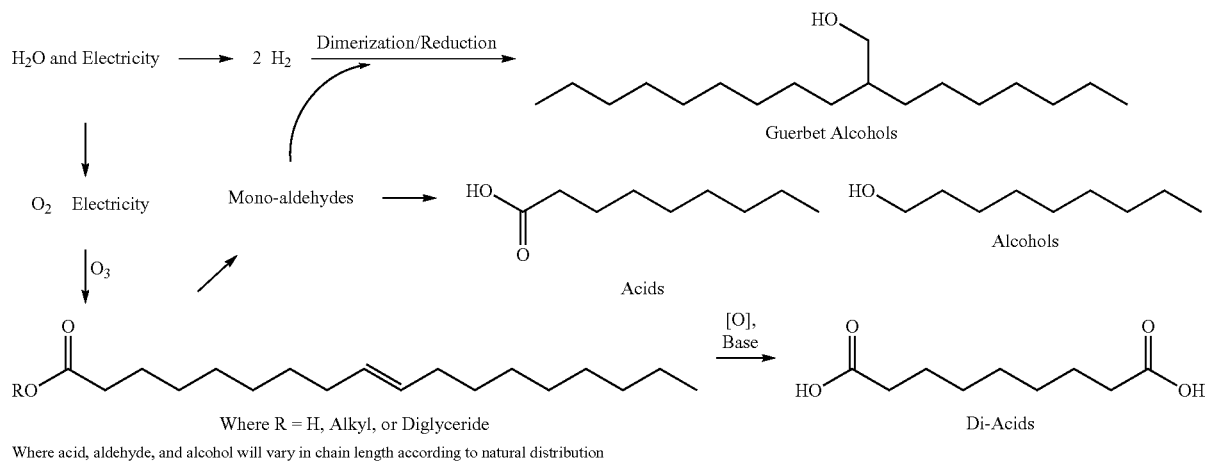

In one embodiment, the mono-aldehyde, which is not consumed for making the enal compound of formula I via dimerization, can be used to synthesize acids, alcohols, amines, esters, and/or amides using known oleochemical transformations. See, e.g., Scheme 2 above.

In one embodiment, the byproduct of the ozonolysis of TG/FA/FAE can be processed to generate di-functionalized alkyl chains, glycerol, and/or glycerol products. See, e.g., Scheme 2 above.

In one embodiment, the ozone used in the ozonolysis is generated by electrolyzing water. Further, the hydrogen generated from electrolyzing water can be used in the reduction step of the dimerization product to produce the target Guerbet alcohol. Alternatively, the hydrogen generated from electrolyzing water can be used in or used to reduce the mono-aldehyde. See, e.g., Scheme 2 above.

The invention further relates to a method of synthesizing a compound of formula IV below:

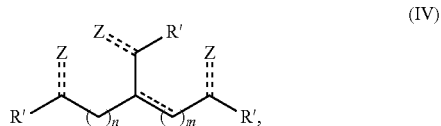

or a salt thereof, wherein
----- is a single or double bond,
each ----- is a double bond or absent, each Z independently is O or S when ----- is a double bond, or Z is absent when ----- is absent, each R' independently is $OR_a$ or $NR_aR_b$, each of $R_a$ and $R_b$, independently, being H, $C_1$-$C_{10}$ alkyl, $C_3$-$C_8$ cycloalkyl, aryl, or heteroaryl, and each of m and n, independently, is 1, 2, 3, 4, 5, 6, 7, 8, 9, 10, 11, or 12.

The method includes reacting $R_x$—CH$_2$CHO with $R_y$—CH$_2$CHO, in which each $R_x$ and $R_y$ independently is substituted $C_1$-$C_{20}$ alkyl containing —COOH at the terminus of the alkyl chain. $R_x$ and $R_y$ can be the same or different. The method may further include reduction, oxidation, amidization, exchanging S and O atoms to form thioketones, and/or forming a salt.

As illustrated in Scheme 3 below, the methods can be used to synthesize novel compounds from vegetable-derived aldehydes. Following the reductive ozonolysis of vegetable oils, acid-aldehydes such as azelaldehyde (i.e., 9-oxononanoic acid) can be generated. These acid-aldehydes can then be dimerized (as shown in Scheme 3 below), or can be condensed with a variety of other aldehydes, such as glyoxylic acid and its derivatives. Following condensation, these compounds can then be derivatized to generate triacids, diacidols, triols, and any amine variants thereof as illustrated in Scheme 3 below (in which R is H, or a cation such as Li$^+$, Na$^+$, or any other suitable metal, ammonium, or phosphonium species, and ----- indicates a single or double bond).

Scheme 3

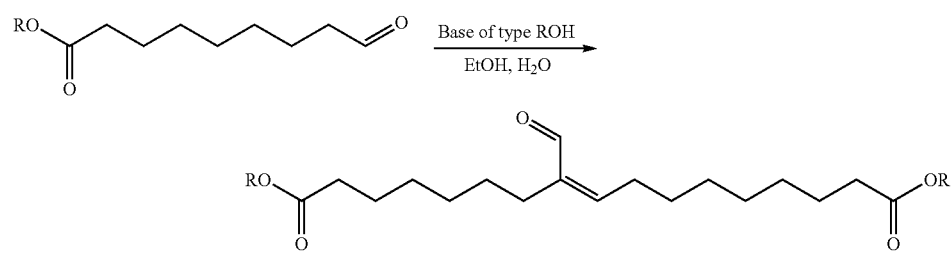

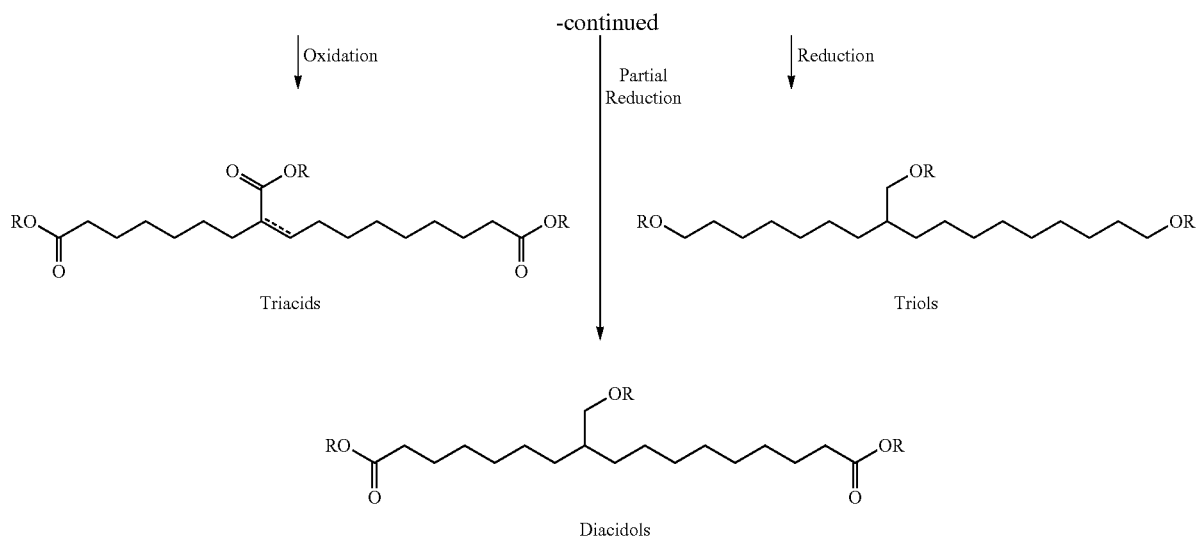

It is understood that the alkyl chain as shown in Schemes 1-3 can be replaced with other alkyl chains with different length depending on the starting material, e.g., biologically derived triglycerides (TG), fatty acids (FA), or fatty acid esters (FAE).

In one embodiment, the mono-aldehydes for dimerization are generated by treating TG/FA/FAE with ozone, followed by distillation or low-pressure removal of the desired aldehydic materials. These aldehydic materials can then passed over a suitable acid or base catalyst, either homo- or heterogeneous in nature, and either organic or inorganic in nature, to facilitate the desired dimerization event.

In one embodiment, trifunctional derivatives can also be obtained using conditions similar to those described above. See, e.g., Scheme 3 above. For example, 9-oxononanoic acid (i.e., azelaldehyde) obtained from the ozonolyitic cleavage of vegetable oil is used as starting material, either in pure form or combined with fatty acids such as pelargonic, palmitic, and stearic acids. The dimerization of azeladehyde can be performed in water as the only solvent. For example, a mixture containing azelaldehyde (e.g., ~41.9% by wt.) and fatty acids is dissolved in water (e.g., 25 mL) in the presence of NaOH (e.g., 28% wt./wt. of azelaldehyde) and the resulting mixture is stirred at, e.g., 70° C., for 1 hour. To determine reaction completion, an analytical aliquot is taken and neutralized with 1 N HCl. Upon neutralization an organic phase separates which can then portioned and used for $^1$H NMR analysis. In one embodiment, at desired level of reaction completion, the basic aqueous solution of the dimer is taken on directly to hydrogenation, either as is, or as diluted aqueous solution. For example, the dimer product is diluted in water (e.g., 300 mL) and charged with Raney Nickel (e.g., 10%-30%, 15-25%, or 20% wt/wt) and the resulting mixture can be placed in a high pressure reactor, and vigorously stirred under a high pressure of $H_2$ and a high temperature (e.g., under about 300-500 psi of $H_2$ and at about 120-200° C.) for about 3-24 hours to obtain the desired alcohol product.

The alcohol product (e.g., triols or diacidols in Scheme 3 above) from the reduction reaction can be >80% pure (e.g., >90%, >95%, >98%, or >99% pure) with >70% yield (e.g., >75%, >80%, >85%, >90%, >95%, >98%, or >99% yield). $^1$H NMR and gas chromatography can be used to characterize the desired alcohol product. For example, disappearance of the enal protons and the appearance of methylene protons at ~3.3-3.5 ppm in $^1$H NMR can show the conversion of the dimer starting material to the desired alcohol product. For example, the alcohol product is free of undesired byproduct or starting material. For example, the impurities (e.g., undesired byproduct or starting material) in the alcohol product is less than 20% (e.g., <10%, <5%, <2%, or <1%).

In one version of the invention, water is used as an oxygen source instead of air for ozone generation, and the molecular hydrogen co-product can be used in the reduction of downstream materials.

In some embodiments, the product of the method of the invention has an overall yield of no less than 60%, e.g., no less than 70%, no less than 80%, or no less than 90%.

The invention also relates to Guerbet alcohol precursors (e.g., compounds of formula I) and Guerbet alcohols (e.g., compounds of formula II) synthesized from the processes described herein.

In some embodiments, the product of the method of the invention contains more than 80% of compound of formula I. In some embodiments, the product of the method of the invention contains more than 85%, 90%, 92%, 95%, 97, or 99% of compound of formula I. For example, the product is free of undesired byproduct or starting material. For example, the impurities (e.g., undesired byproduct or starting material such as mono-aldehyde) in the alcohol product is less than 20% (e.g., <15%, <10%, <8%, <5%, <3%, <2%, or <1%).

In some embodiments, the product of the method of the invention contains more than 80% of compound of formula II. In some embodiments, the product of the method of the invention contains more than 85%, 90%, 92%, 95%, 97, or 99% of compound of formula II. For example, the product is free of undesired byproduct or starting material. For example, the impurities (e.g., undesired byproduct or starting material such as aldehyde dimer) in the product is less than 20% (e.g., <15%, <10%, <8%, <5%, <3%, <2%, or <1%).

It will be appreciated that the methods disclosed herein are suitable for both large-scale and small-scale preparations of the desired compounds. In preferred embodiments of the methods described herein, the enal compounds of formula I or compounds of formula II may be prepared on a large scale, for example on an industrial production scale rather than on an experimental/laboratory scale. For example, a batch-type process according to the methods of the disclosure allows the preparation of batches of at least 1 g, or at least 5 g, or at least 10 g, or at least 100 g, or at least 1 kg, or at least 10 kg, or at least 100 kg of product. Furthermore, the methods allow the preparation of a product having a purity of at least 80%, at least 85%, at least 90%, at least 95%, at least 98%, or at least 98.5%. For example, the product is free of undesired byproduct or starting material. For example, the impurities (e.g., undesired byproduct or starting material such as mono-aldehyde or aldehyde dimer) in the product is less than 20% (e.g., <15%, <10%, <8%, <5%, <3%, <2%, <1.5%, or <1%).

The compounds described herein can be prepared by the methods of the invention. Alternatively and additionally, the compounds described herein can be prepared by the methods described in, e.g., co-owned U.S. Provisional Application Nos. 61/668,863 filed Jul. 6, 2012; 61/673,411, filed on Jul. 19, 2012; and 61/784,376, with the title "Ozonolysis Operations for Generation of Reduced and/or Oxidized Product Streams"; and U.S. Pat. Nos. 6,093,856; 6,060,443; 6,013,813; 6,008,181; 5,929,263; 5,919,959; 5,919,743; 5,786,389; 5,756,785; 5,744,626; 5,717,119; 5,646,321; 5,488,121; 5,387,374; 5,312,968; 5,264,006; 5,094,667; 4,830,769; 4,800,077; 4,767,815; 4,731,190; and 4,425,458. Suitable methods for preparing the compounds described herein can also be found in, e.g., M. Guerbet, C. R. *Acad. Sci. Paris,* 128, 511; 1002 (1899); Veibel, S and Nielsen, J., *Tetrahedron,* 23, 1723-1733 (1967); S. Cannizzaro, *Liebigs Ann. Chem.* 88, 129, (1853); Geissman, T. A., *Organic Reactions*, Vol II, p. 94 Wiley, New York (1944); O'Lenick, Jr. Anthony J. and Bilbo, Raymond E., *Guerbet Alcohols, Versatile Hydrophobes*, SCCS, April, 1987; Henkel, K., *Fatty Alcohols, Raw Materials, Process and Applications*, Henkel KGaA, 1982, p. 163; Stein, W. in: *Method Chim.* 5 (1975) p. 563-573; German Patent No. 538,388 October 1931; Morrison, Robert and Boyd, Robert, *Organic Chemistry*, 3rd Edition, (1973) p. 582; O'Lenick, Anthony *J. Surfactants Chemistry and Properties*, Allured Publishing, 1999, p. 28-30; Sunwoo, Chunkee, and Wade, William H., *J. Dispersion Sci and Tech,* 13, 491, 1992.

The details of one or more embodiments of the invention are set forth in the accompanying description below. Unless defined otherwise, all technical and scientific terms used herein have the same meaning as commonly understood by one of ordinary skill in the art to which this invention belongs. In the case of conflict, the present specification will control.

Unless otherwise indicated, it is to be understood that the terminology used herein is for the purpose of describing particular embodiments only and is not intended to be limiting. In this specification and in the claims that follow, reference will be made to a number of terms, which shall be defined to have the definitions set forth below.

As used herein, the singular forms "a," "an," and "the" include plural referents unless the context clearly dictates otherwise. Thus, for example, reference to "a reactant" includes not only a single reactant but also a combination or mixture of two or more different reactant, reference to "a substituent" includes a single substituent as well as two or more substituents, and the like.

As used herein, the phrases "for example," "for instance," "such as," or "including" are meant to introduce examples that further clarify more general subject matter. These examples are provided only as an aid for understanding the disclosure, and are not meant to be limiting in any fashion.

Furthermore as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

As used herein, the phrase "having the formula" or "having the structure" is not intended to be limiting and is used in the same way that the term "comprising" is commonly used.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Calm et al., *Experientia* 1956, 12, 81; Cahn, *J. Chem. Educ.* 1964, 41, 116). In some formulae of the present application, one or more chiral centers are identified by an asterisk placed next to the chiral carbon. In other formulae, no chiral center is identified, but the chiral isomers are nonetheless covered by these formulae.

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Some compounds of the present invention can exist in a tautomeric form which is also intended to be encompassed within the scope of the present invention. "Tautomers" refers to compounds whose structures differ markedly in arrangement of atoms, but which exist in easy and rapid equilibrium. It is to be understood that the compounds of the invention may be depicted as different tautomers. It should also be understood that when compounds have tautomeric forms, all tautomeric forms are intended to be within the scope of the invention, and the naming of the compounds does not exclude any tautomeric form. Further, even though one tautomer may be described, the present invention includes all tautomers of the present compounds.

As used herein, the term "salt" can include acid addition salts including hydrochlorides, hydrobromides, phosphates, sulfates, hydrogen sulfates, alkylsulfonates, arylsulfonates, acetates, benzoates, citrates, maleates, fumarates, succinates, lactates, and tartrates; alkali metal cations such as $Na^+$, $K^+$, $Li^+$, alkali earth metal salts such as $Mg^{2+}$ or $Ca^{2+}$, or organic amine salts, or organic phosphonium salts.

The term "alkyl" as used herein refers to a branched or unbranched saturated or unsaturated hydrocarbon group typically although not necessarily containing 1 to about 28 carbon atoms, such as methyl, ethyl, n-propyl, isopropyl, n-butyl, isobutyl, t-butyl, octyl, decyl, and the like. Generally, although not necessarily, alkyl groups in the lipids described herein may contain 4 to about 28 carbon atoms, and such groups may contain 10 to about 28 carbon atoms. "Substituted alkyl" refers to alkyl substituted with one or more substituent groups, and the terms "heteroatom-containing alkyl" and "heteroalkyl" refer to an alkyl group in which at least one carbon atom is replaced with a heteroatom such as O, S, Se, N, or P.

As used herein, the term "cycloalkyl" is intended to include saturated or unsaturated nonaromatic hydrocarbon rings having 3 to 30 carbon atoms. The term "$C_3$-$C_8$ cycloalkyl" thus refers to a cycloalkyl having 3, 4, 5, 6, 7, or 8 carbon atoms in its ring structure. In one embodiment, a cycloalkyl group has five or six carbons in the ring structure, such as cyclopentyl, cyclopentenyl, cyclohexyl and the like. "Substituted cycloalkyl" refers to cycloalkyl substituted with one or more substituent groups, and the terms "heteroatom-containing cycloalkyl" and "heterocycloalkyl" refer to an cycloalkyl ring in which at least one carbon atom is replaced with a heteroatom.

"Aryl" includes groups with aromaticity, including "conjugated" or multicyclic, systems with at least one aromatic ring. Examples include phenyl, benzyl, etc.

"Heteroaryl" groups are aryl groups, as defined above, having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthyridine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged. Cycloalkyl, heterocycloalkyl, aryl, and heteroaryl can also be fused with each other. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

By "substituted" as in "substituted alkyl," and the like, it is meant that in the alkyl, or other moiety, at least one hydrogen atom bound to a carbon atom is replaced with one or more non-hydrogen substituents, e.g., by a functional group.

Examples of functional groups include, without limitation: halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—$N^+$≡$C^-$), cyanato (—O—C≡N), isocyanato (—O—$N^+$≡$C^-$), isothiocyanato (—S—C≡N), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)($O^-$)), phospho (—$PO_2$), -phosphino (—$PH_2$), mono- and di-($C_1$-$C_{24}$ alkyl)-substituted phosphino, mono- and di-($C_5$-$C_{20}$ aryl)-substituted phosphino; and the hydrocarbyl moieties such as $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties such as those specifically enumerated above.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention.

All percentages and ratios used herein, unless otherwise indicated, are by weight.

EXAMPLES

Example 1: Dimerization of Long-chain Aliphatic Aldehydes

A process for the dimerization of oleochemical-derived aldehydes has been developed using ethanol:water solutions as reaction media to obtain specific solubilization requirements of both starting materials and products. Specifically, starting aldehydes were first soluble in the basic reaction media and were converted to the dimer successfully in high yield. Following conversion, the desired products were phase separated from the reaction media for facile isolation.

Experimental

Representative Procedure for Data Generated in Tables 1 and 2.

Hexanal or nonanal was added to a solvent, i.e., an ethanol aqueous solution charged with 1.35 g of NaOH at 70° C. to result in a total volume of 50 mL. As indicated in Table 1 below, the volumetric ratio of ethanol to water in the solvent ranged from 99:1 to 0:100, and the volumetric ratio of the solvent to the aldehyde was kept at 9:1. In comparison, as indicated in Table 2 below, the volumetric ratio of ethanol to water in the solvent was kept at 50:50, and the volumetric ratio of the solvent to the aldehyde ranged from 9:1 to 1:1. The mixture was vigorously stirred via overhead stirring at 660 RPM for fifteen minutes at 70° C. After fifteen minutes, an aliquot of the reaction mixture was taken and quenched into 1.0 M hydrochloric acid. The aliquot was diluted with water and the organics were extracted with deuterated chloroform, from which proton NMR was taken. The remaining reaction mixture was subsequently poured into a graduated cylinder and observation of reaction mixture phase separation was noted.

Table 1, below, outlines the conversion and subsequent separation of the enal products in selected ethanol:water systems (Note: preferred solvent systems will possess a "+/+" designation).

TABLE 1

Dimerization conversion and subsequent phase separation of alkyl aldehydes in 9:1, solvent:substrate systems.*

| Solvent Ethanol:Water | Substrate (conversion/phase separation)** | |
| --- | --- | --- |
| volumetric ratio | Hexanal | Nonanal |
| 99:1 | +/− | +/− |
| 95:5 | +/− | +/− |
| 75:25 | +/− | +/+ |
| 50:50 | +/+ | +/+ |
| 0:100 | −/+ | −/+ |

*Reaction conditions include 2.7% wt/vol NaOH, stirring at 70° C. and 660 rpm for 15 minutes.
**"+" indicates >90% conversion to desired product by $^1$H NMR on the left of the slash whereas <90% conversion is indicated with a "−". Further, a "+" indicates that rapid phase separation was observed and a "−" indicates that phase separation was not observed when referring to phase separation. For example, a "+/+" designation indicates that >90% conversion and rapid phase separation was observed.

Additionally, preferred ethanol:water solvent systems were used at varying solvent:substrate volumetric ratios while maintaining desirable conversion and phase separation, as indicated in Table 2. Surprisingly, the desirable conversion and separation were maintained when the basic solution:aldehyde volumetric ratio increased from 9:1 to 1:1.

TABLE 2

Dimerization conversion and subsequent phase separation of alkyl aldehydes with varying solvent:substrate, where solvent is 1:1, ethanol:water.*

| Solvent:Aldehyde | Substrate (conversion/phase separation)** | |
| --- | --- | --- |
| volumetric ratio | Hexanal | Nonanal |
| 9:1 | +/+ | +/+ |
| 4:1 | +/+ | +/+ |
| 1:1 | +/+ | +/+ |

*Reaction conditions include 2.7% wt/vol NaOH, stirring at 70° C. and 660 rpm for 15 minutes.
**"+" indicates >90% conversion to desired product by $^1$H NMR on the left of the slash and a "+" on the right of the slash indicates that rapid phase separation was observed. For example, a "+/+" designation indicates that >90% conversion and rapid phase separation was observed.

The role of conversion in phase separation was further investigated by setting up control experiments where base was omitted from the solvent system so that no reaction would take place. The results are shown in Table 3, where a "+" indicates that rapid phase separation was observed and a "−" indicates that phase separation was not observed. For example, a "+/−" designation indicates that conversion products (i.e. the enal dimer) readily phase separated whereas the starting material (i.e. hexanal and/or nonanal) did not phase separate from the reaction media.

TABLE 3

Dimerization phase separation versus non-basic control experiment of alkyl aldehydes in 9:1, solvent:substrate systems.*

| Solvent | Substrate (phase separation) | |
| --- | --- | --- |
| (Ethanol:Water) | Hexanal (Base/No Base) | Nonanal (Base/No Base) |
| 95:5 | −/− | −/− |
| 75:25 | −/− | +/− |
| 50:50 | +/− | +/+ |
| 0:100 | +/+ | +/+ |

*Basic reaction conditions include 2.7% wt/vol NaOH, stirring at 70° C. and 660 rpm for 15 minutes for dimerization experiments. Non-basic reactions were identical save that NaOH was excluded.

A representative $^1$H NMR of the dimer can be seen in FIG. 1. Characteristic peaks for the enal functional groups, i.e., ~9.34 ppm (singlet) and ~6.57 ppm (triplet), were observed.

Example 2: Reduction of Product from Dimerization 250 mL of nonanal (206 g, 1.45 mol) was dimerized according to the aforementioned conditions in Example 1, and the resulting dimer was separated from the ethanol and water layer. The dimer was then charged with 20% wt/wt Raney Nickel. The resulting mixture was placed in a high pressure reactor and was vigorously stirred under 300 psi of $H_2$ at 125° C. for 24 hours. The resulting material was then filtered to remove catalyst, yielding >90% pure desired product in >80% yield. $^1$H NMR of the product was characterized by the disappearance of the enal protons and the appearance of 2 methylene protons at ~3.3-3.5 ppm.

Example 3: Dimerization of Nonanal and Reduction of Dimer

Nonanal derived from the ozonolytic cleavage of fatty acid (7 mL, 5.789 g) was diluted with 10 mL of a 1:1, ethanol:water solution charged with sodium hydroxide (3.4% by wt.). The reaction was then stirred for 15 minutes at 70° C. and then removed from heat and stirring to allow for phase separation in a separatory funnel.

Figure 2:
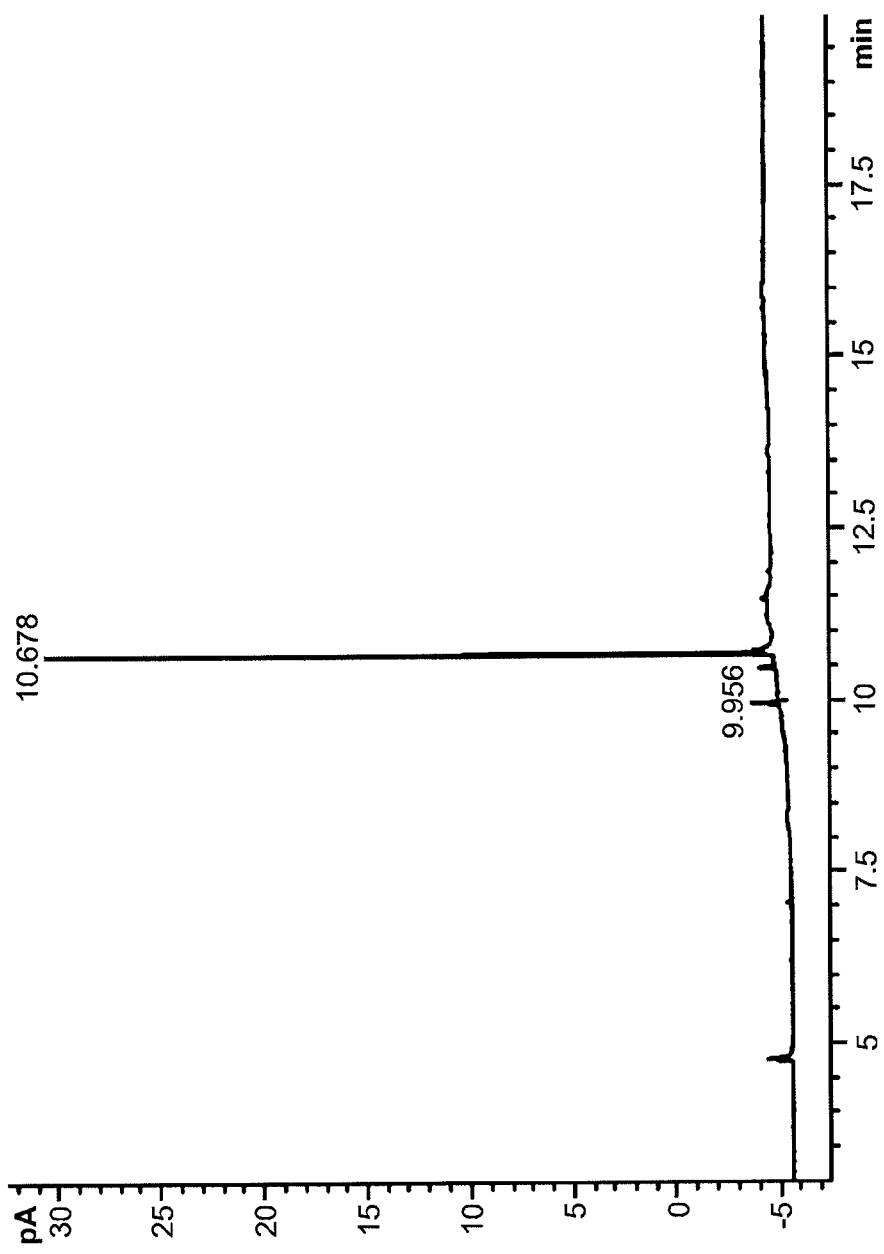
FIG. 2 is a diagram showing gas chromatography (GC) flame ionization detector (FID) analysis following the dimerization of nonanal.

The top, organic phase was then taken on directly for reduction (5.529 g). An analytical aliquot of this material was taken for GC FID analysis, the result of which is shown in FIG. 2. The dimer peak was at 10.678 min. A peak indicating a trace of the starting material, nonanal, was observed at ~4.7 minutes. This trace suggested >95% conversion to desired product.

Figure 3:
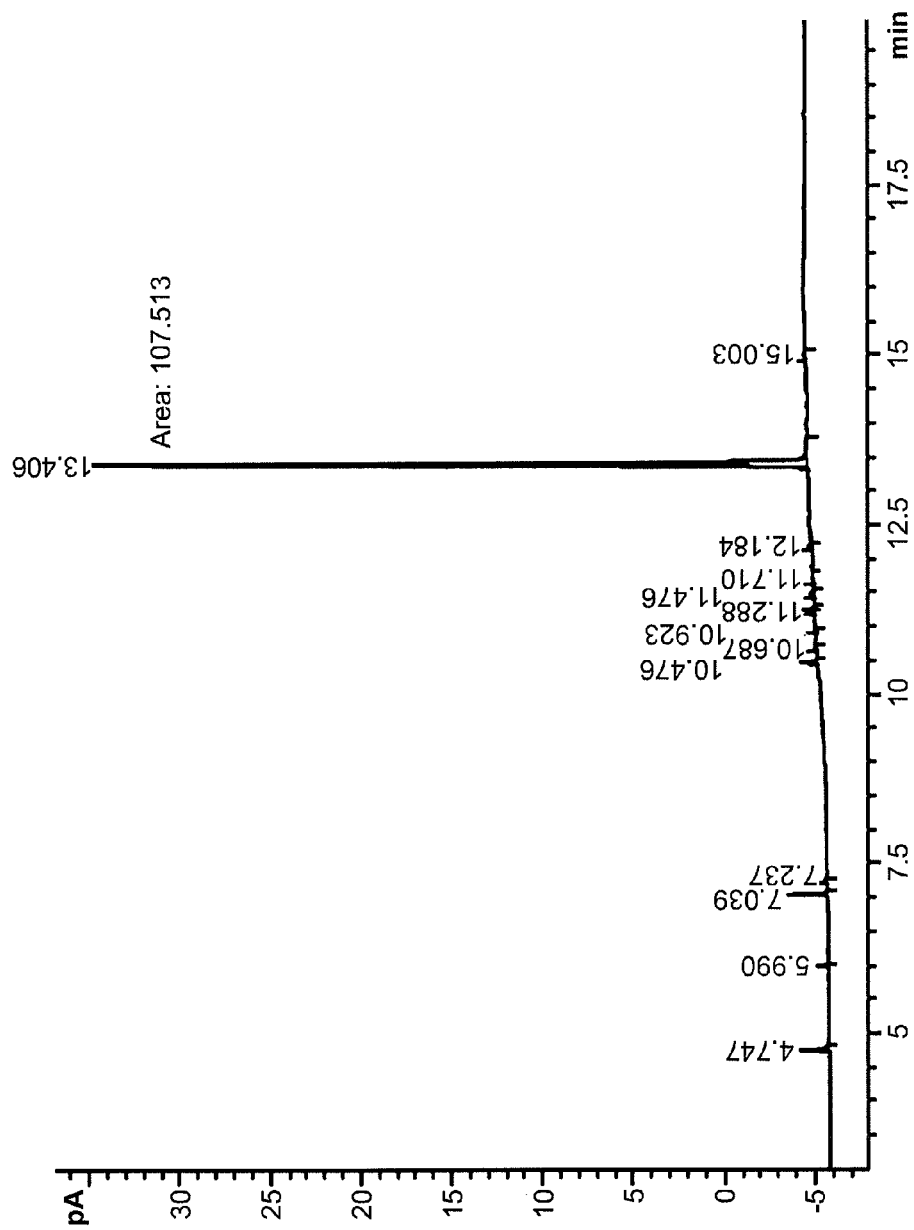
FIG. 3 is a diagram showing GC FID analysis following the reduction of the nonanal dimer to the desired alcohol.

The organic phase was then diluted in ethanol (300 mL) and charged with Raney Nickel (20% wt/wt) in a Parr hydrogenation apparatus. The reactor was sealed and charged with 420 psi hydrogen gas at 160° C. for 3 hours. The reaction was then cooled, catalyst was filtered off, and solvent was removed. 5.4 g organic material was recovered. An analytical aliquot of the organic material was analyzed using GC FID. The desired alcohol peak was at 13.406 min of the GC FID trace. The result shown in FIG. 3 suggests that the desired alcohol was >90% pure.

Example 4: Trifunctional Derivatives 5 g of azelaldehyde as ~41.9% by wt. in a mixture with fatty acids was dissolved in 25 mL of water in the presence of 1.39 g of NaOH. The resulting solution was stirred at 70° C. for 1 hour. An analytical aliquot was taken and neutralized with 1 N HCl. Upon neutralization an organic phase separated which was then portioned and used for $^1$H NMR analysis. The $^1$H NMR data indicated the formation of the characteristic enal functional groups, as well as the disappearance of other aliphatic aldehydes.

The basic aqueous solution was then taken on directly to hydrogenation, either with or without dilution to form an aqueous solution. In one experiment, 5 g of reacted material was diluted in 300 mL of water and charged with Raney Nickel (20% wt./wt.). The resulting mixture was then placed in a high pressure reactor and was vigorously stirred under 400 psi $H_2$ pressure at 160° C. for 3 hours. After filtration and neutralization, an analytical sample was used for $^1$H NMR analysis, which indicated the disappearance of the characteristic enal protons, as well as the appearance of the characteristic methylene proton at ~3.3 to 3.5 ppm, consistent with formation of the desired 8-(hydroxymethyl)heptadecanedioic acid.

INCORPORATION BY REFERENCE

The entire disclosure of each of the patent documents and scientific articles referred to herein is incorporated by reference for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of producing a compound of formula I:

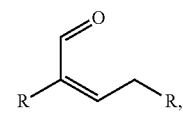

or a salt thereof, wherein each R independently is hydrogen or unsubstituted or substituted C1-C20 alkyl, wherein the alkyl is linear or branched and optionally contains a carbonyl moiety (C═O) within or at the terminus of the alkyl chain, the method comprising:
    ozonolysis of a triglyceride, a fatty acid, or a fatty acid ester to obtain a mono-aldehyde having the formula R—CH2CHO; and
    dimerizing the mono-aldehyde to obtain the compound of formula I, wherein the dimerization reaction is performed in an alcohol aqueous solution.

2. The method of claim 1, further comprising, between ozonolysis and dimerization steps, isolating the mono-aldehyde from other ozonolysis products by distillation.

3. The method of claim 2, wherein the distillation is performed under vacuum.

4. The method of claim 1, wherein each R independently is alkyl having 1, 2, 3, 4, 5, 6, 7, 8, 9, 10, 11, 12, 13, 14, 15, or 16 carbon atoms.

5. The method of claim 1, wherein each R independently is alkyl having 2, 3, 4, 5, 6, 7, 8, 9, or 10 carbon atoms.

6. The method of claim 1, wherein the dimerization reaction is performed in the presence of an acid or base.

7. The method of claim 1, wherein the volume ratio between the alcohol and water in the alcohol aqueous solution ranges from 10:1 to 1:10.

8. The method of claim 7, wherein the alcohol is ethanol.

9. The method of claim 1, wherein the ozone used in the ozonolysis step is generated by electrolyzing water.

10. The method of claim 9, wherein hydrogen generated by electrolyzing water is used in the reduction of the compound of formula I to produce a compound of formula II:

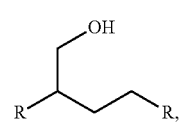

or a salt thereof.

11. The method of claim 1, wherein each R independently is hydrogen, unsubstituted C1-C20 alkyl, or substituted C1-C20 alkyl containing —COOH at the terminus of the alkyl chain.

12. The method of claim 1, wherein each R independently is alkyl having 4, 5, 6, 7, 8, 9, or 10 carbon atoms.

* * * * *